United States Patent
Arahira et al.

(10) Patent No.: US 6,492,114 B2
(45) Date of Patent: *Dec. 10, 2002

(54) METHOD FOR PREPARING TEMPLATE DNA FROM PROCESSED VEGETABLE FOOD, WHICH IS FEASIBLE FOR AMPLIFICATION OF DNA REGION BY PCR METHOD

(75) Inventors: Masaomi Arahira, Tsukuba (JP); Chikafusa Fukazawa, Tsukuba (JP)

(73) Assignees: Director of National Food Research Institute, Tsukuba (JP); Ministry of Agriculture, Forestry and Fisheries, Tsukuba (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/494,438

(22) Filed: Jan. 31, 2000

(65) Prior Publication Data

US 2002/0037504 A1 Mar. 28, 2002

(30) Foreign Application Priority Data

Nov. 26, 1999 (JP) .......................................... 11-336142

(51) Int. Cl.⁷ .......................... C12Q 1/68; C12P 19/34; C07H 21/02; C07H 21/04; C07H 21/00
(52) U.S. Cl. .......................... 435/6; 435/91.1; 435/91.2; 536/23.1; 536/24.3; 536/25.4; 536/25.41
(58) Field of Search .......................... 435/6, 91.1, 91.2, 435/183; 436/94; 536/23.1, 24.3, 24.33, 25.3, 25.4, 25.41

(56) References Cited

U.S. PATENT DOCUMENTS 3,900,288 A * 8/1975 Levine .......................... 21/58
4,548,831 A * 10/1985 Iwamura ........................ 426/634
5,707,796 A * 1/1998 Gold et al. ...................... 435/6

FOREIGN PATENT DOCUMENTS

JP     56137861     * 10/1981

OTHER PUBLICATIONS

Zlmmermann et al., Quantitative and qualitative evaluation of nine different extraction methods for nucleic acids on soya bean food samples. Z Lebensm Unters Forsch A 207, 81–90, 1998.*

Van Hoef et al., Development and application of a selective detection method for genetically soy and soy–derived products. Food Additives and Contaminants. 15, 767–774, Oct. 1998.*

Marino et al., Molecular size determinations of DNA restriction fragments and polymerase chain reaction products using capillary gel elctrophoresis. J. Chromatograph A 676, 185–189, 1994.*

Zlemmermann et al., Quantitative and qualitativen evaluation of nine different extraction methods for nucleic acids on soy bean food samples. Z Lebensm Unters Forsch A 207, 81–90, 1998.*

Van Hoef et al., Developement and application of a selective detection method for genetically soy and soy–derived products. Food Additives and Contaminants. 15, 767–774, 1998.*

Promega Catalog (1999), p. 20.14. Published by Promega, 2800 Woods Hollow Road, Madison, WI 57711–5399, USA, 1999.*

Zlmmermann et al., Quantiative and qualitative evaluation of nine different extraction methods for nucleic acids on soya bean food samples. Z Lebensm Uters Forsch A 207, 81–90, 1998.*

Van Hoef et al., Developement and application of a selective detection method for genetically soy and soy–derived products. Food Additives and Contaminants. 15, 767–774, 1998.*

Organic Chemistry Book, second edition (1991), pp. 1150 and 1151. Edited by L. G. Wade, Jr., Published by Prentice Hall, Englewood Cliffs, New Jersey 07632.*

Maniatis et al., Molecular Cloning: A Laboratory Manual, p. 164, 1982. Published by Cold Spring Harbor Laboratory, Box 100, Cold Spring Harbor, New York.*

Promega Protocol and Applications Guide (1996), Third Edition, pp. 87–89, Cat.#P1610. Published by Promega, 2800 Woods Hollow Road, Madison, WI 53711–5399, USA.*

* cited by examiner

*Primary Examiner*—Ethan C. Whisenant
*Assistant Examiner*—Frank Lu
(74) *Attorney, Agent, or Firm*—Oblon, Spivak, McClelland, Maier & Neustadt, P.C.

(57) ABSTRACT

Disclosed is a method for preparing a template DNA from a processed vegetable food, comprising the steps of: extracting a crude DNA fraction from a processed vegetable food subjected to at least one of a high temperature treatment, a high temperature grinding treatment, a high pressure treatment and a fermentation treatment, and optionally subjected to defatting; and performing a DNA fractionation treatment of the crude DNA fraction by a polyethylene glycol precipitation method and/or a polyacrylamide gel electrophoresis method. Also disclosed is a method for detecting a gene of a plant in a processed vegetable food derived from the plant by a PCR method in which such a template DNA is used. The processed vegetable food may be an oil source seed.

5 Claims, 3 Drawing Sheets

SEQUENCE LISTING

<160> NUMBER OF SEQ ID NOS: 11

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 1
ttgtgttgga ttctggggat ggtgtcagcc                                    30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 2
ttcctagcat cgctgataga atgagcaagg                                30

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 3
atttctgctt tagccccaag tagcatgaag                                30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 4
aactgctgga aggtgcttag agatgcaagg                                30

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 5
gatcctccaa tccaaacacc gaactttctc                                30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 6
caaatcctct ggcctttccg gaaccgtccg                                30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 7
gacaagtcga tctcccaccg gtccttcatg                                30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 8

-continued

```
cgcggagttc ttccagaccg ttcatcacgg                                      30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 9
gcgacagcga gaatcggata ttcgtcgatc                                      30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 10
cgagcttccc ggagttcatg gacctgatgg                                      30

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 11
catgcttaac gtaattcaac agaaattata tg                                   32
```

METHOD FOR PREPARING TEMPLATE DNA FROM PROCESSED VEGETABLE FOOD, WHICH IS FEASIBLE FOR AMPLIFICATION OF DNA REGION BY PCR METHOD

FIELD OF THE INVENTION

The present invention relates to a method for preparing a template DNA from a processed food using seeds of a plant such as soybean as a material, the template DNA being usable for detecting the genes of the plant and recombinant genes thereof by a PCR method and to a method for detecting the genes of a plant using such a template DNA in detecting the genes of the plant in the processed vegetable food derived from the plant by a PCR method.

Processed food using seeds of a plant as a material are subject to high temperature treatment, high temperature grinding treatment, high pressure treatment, or mechanical grinding treatment during the process of its production and as a result fragmentation of DNA molecule occurs. In the case of fermented foods such as bean paste and fermented soybeans, further fragmentation of DNA occurs due to nuclease originated from microorganisms.

The present invention is to provide a method for preparing a DNA fragment having a purity capable of using as a template for PCR amplification from such a processed vegetable food. Further, the present invention is to provide a method for using said template DNA in detecting by a PCR method the genes of a plant from which processed vegetable food is produced.

BACKGROUND OF THE INVENTION

For the extraction of plant DNAs, i.e., DNAs of soybean and other plants, there have already been developed fundamental techniques, which can also be used for the extraction of DNA from foods, such as the CTAB method (Marray, M. G. and Thompson, W. F. (1980); Rapid isolation of high molecular weight plant DNA. Nucleic Acids Res., 8, 4321–4325), the SDS-phenol method (David, R. W., Thomas, M., Cameron, J., St. John, T. P., Scherer, S. and Padgett, R. A.; (1980) "Methods in Enzymology", ed. by Grossman, L. and Moldav, K., Vol. 65, p404, Academic Press, New York), and the protease K method (Jofuku, K. D., Goldberg, R. B.; (1988) Plant molecular biology—a practical approach, ed. by Show, C. H., p37, IRL Press, Oxford-Washington D.C.).

However, when processed foods using plant seeds as a material are produced, generally the material is often subjected to various processing steps such as high temperature, high pressure, and mechanical grinding treatments, or fermentation operation with microorganisms. For this reason, if the above fundamental techniques are applied directly, it has been in many cases difficult to prepare a DNA having a sufficient purity to be used as a template DNA in PCR amplification.

For example, in the case of soybean, which is one of materials for Japanese traditional plant-derived foods, seeds and bean sprouts allow extraction of high purity DNA which is in a native state only by use of the above fundamental methods. Tofu (bean curd) inclusive of kori-dofu (freeze-dried tofu) and aburaage (fried tofu slice) inclusive of ganmodoki (fried stuffed tofu), etc. can be used for preparing a template DNA for PCR by use of the above fundamental methods without pretreatment or DNA purification operation since they have undergone DNA fragmentation during their production, although yield of the template DNA is low.

In the case of kinako (parched bean flour) (high temperature grinding) and steamed/boiled soybean (cooked bean, autoclaving), or their fermented foods (natto (fermented soybeans), miso (bean paste), etc.) and the like, the DNA is cut into fragments by the respective treatment involved and hence it has been very difficult to prepare high purity DNA with which no low molecular weight DNA is mixed.

SUMMARY OF THE INVENTION

The first object of the present invention is to provide a method for preparing high purity DNA which can be used as a template for PCR from processed vegetable foods derived from soybean and other plant seeds as a material, the processed foods having been subjected to denaturation treatment for protein.

Another object of the present invention is to provide a method for detecting a gene of a plant by a PCR method from a processed vegetable food derived from the plant, using said template DNA.

To know exactly what the materials contained in a highly processed food are like is now a global trend in the stream of consumers' consciousness. However, many of the operations during the processing procedure are often accompanied by considerable denaturation of proteins so that the identification of plant materials by the analysis of proteins according to the conventional methods were successful in only limited situations.

In order to obviate the above problems, the present inventors have made intensive research and as result they have found that use of optional pretreatment prior to fundamental methods for DNA extraction and application of specified purification and separation methods after the extraction enable preparation of high purity DNA even from processed vegetable foods which has been subjected to a protein denaturation treatment.

Thus, if DNA which is resistant to heat treatment and the like, that is, remains in the processed food in an uncleaved state after the protein denaturation treatment can be prepared in a highly pure state, then it is possible to clarify the name of the plant material with high sensitivity by detecting the gene of the plant by a PCR method using this. Finally, there is the possibility that a judgment can be realized as to whether or not the plant as a raw material of processed vegetable food is a plant that has been subjected to gene recombination treatment. The present invention has been achieved based on these findings.

Therefore, according to a first aspect of the present invention, there is provided a method for preparing a template DNA from a processed vegetable food, comprising the steps of:

extracting a crude DNA fraction from a processed vegetable food subjected to at least one of a high temperature treatment, a high temperature grinding treatment, a high pressure treatment and a fermentation treatment, and optionally subjected to defatting; and performing a DNA fractionation treatment of the crude DNA fraction by a polyethylene glycol precipitation method and/or a polyacrylamide gel electrophoresis method.

According to a second aspect of the present invention, there is provided a method for detecting a gene of a plant in a processed vegetable food derived from the plant by a PCR method, wherein the template DNA obtained by the method of the first aspect of the present invention is used.

According to a third aspect of the present invention, in the method of the second aspect of the invention, the processed vegetable food is an oil source seed.

BRIEF DESCRIPTION OF THE DRAWINGS

FIG. 3 is an electrophoretogram showing the results of Test Example 3, in which character M in the upper part indicates a marker. Numerals 1 to 6 on the left side indicate that the results of non-recombinant genes are concerned and 1 to 6 on the right hand side indicate that the results of recombinant genes are concerned. Numerals 1 to 6 designate soybean seeds, soybean sprouts, soybean curd, fried soybean curd slice, steamed/boiled soybeans, and fermented soybeans, respectively. Numerals on the left side represent molecular weights.

DETAILED DESCRIPTION OF THE INVENTION

Hereafter, the present invention will be described in detail.

The present invention relates to a method for preparing a high purity template DNA from a processed food derived from seeds of a plant, such as soybean as a material, the template DNA being usable for amplifying a DNA region by a PCR method and to a method for using such a template DNA in detecting the genes of the plant in the processed vegetable food by a PCR method.

The object to which the present invention is applied is a vegetable food which has been subjected to a protein denaturation treatment, such as a high temperature treatment, a high temperature grinding treatment, a high pressure treatment or a fermentation treatment.

The protein denaturation treatment includes, for example, a high temperature grinding treatment, an autoclave (high pressure) treatment or fermentation treatment, when the raw material is soybean. Specific examples of the processed foods subjected to such treatments include bean curd, fried bean curd slice, parched bean flour, etc. as examples subjected to a high temperature grinding treatment, steamed/boiled soybean (cooked bean) as an example of an autoclave treatment, fermented soybeans and bean paste as examples subjected to a fermentation treatment in addition to these treatments.

The processed vegetable foods will not give such a high purity DNA as can be used in a PCR method when DNA is extracted by a usual method. This demonstrates the significance of the present invention.

In the above explanation, given is an example of processed food using soybean as a raw material. However, the object to which the present invention is applied to is not limited to processed soybean foods but includes also processed foods prepared from various plants as raw materials, such as potato chips and pop corns, as well as processed foods from rice, wheat, etc.

In the present invention, when a processed vegetable food in which there is the possibility that a genetic recombinant plant is used partly or wholly is selected to be an object, the detection of recombinant gene can be carried out using the obtained DNA.

The method of the present invention is to extract and prepare DNA from processed vegetable foods subjected to the protein denaturation treatments as described above. It performs a defatting treatment of the food as a pretreatment according to its necessity, and then select suitable one from among the above-described fundamental techniques to extract. In particular, plant seeds finely pulverized as they are or those covered with oil or the like must be subjected to a defatting treatment.

Even if a plant tissue such as seed is subjected to a high pressure steaming/boiling treatment, the part of DNA region that is wound around histone core is protected and therefore remains without fragmentation. On the contrary, the DNA chain between nucleosomes is fragmented to a size of several tens bases. In the case of fermented soybeans and bean paste, DNA in nucleosome units is further decomposed by a protease and nuclease derived from fermentation microbes. If such a low molecular DNA is present, the PCR method is inhibited thereby.

In particular, in the case of fermented soybeans, in addition to enzymatic decomposition of DNA fragments, contamination of a large amount of polysaccharide (fructan) produced by Bacillus subtilis (natto-producing bacteria) into DNA preparation occurs, thereby inhibiting PCR amplification considerably. In the case of starch seeds such as corn, partial decomposition of starch due to intracellular amylase during the process of steaming/boiling to generate oligosaccharides, which are also inhibitors to the PCR method.

In the present invention, defatting treatment of processed vegetable food can remove low molecular DNA which causes problems upon PCR to prevent a decrease in purity of DNA to be prepared by a later treatment, so that DNA having a sufficient purity to be provided for PCR amplification can be obtained.

Vegetable foods not subjected to any protein denaturation treatment, such as soybean seeds and bean sprouts, no defatting treatment is necessary.

The defatting treatment can be carried out by a known technique, for example, the Soxhlet method using diethyl ether or the like as a solvent, a defatting treatment using an ether, and the like.

The conditions of defatting treatment may be determined appropriately taking, for example, the kind of processed food into consideration. For example, the temperature of ether layer is set to 65° C. and extraction is carried out for 14 hours.

When DNA is extracted from processed foods using plant oil source seeds, such as soybean, for example, "kinako" (parched bean flour) which is obtained by converting seed itself to fine powder by a high temperature grinding treatment, and processed vegetable food covered with oil, for example, pop corn, the defatting treatment is an essential pretreatment.

In the present invention, in addition to the defatting treatment as a pretreatment, freeze-drying, high pressure treatment such as autoclaving, etc. of processed food as a raw material enables the preparation of target DNA to be carried out effectively.

The conditions of freeze-drying and high pressure treatment are not particularly limited and they may be carried out under ordinary conditions.

Those foods, of which DNA has been decomposed by a protease and/or a nuclease derived from fermentation microorganisms, such as fermented soybeans and bean paste, in particular fermented soybeans, have the possibility that contamination of a large amount of polysaccharide (fructan) produced by Bacillus subtilis (natto-producing bacteria) into DNA will inhibit PCR so that it is preferred that an autoclave treatment be carried out to sterilize it and further after a freeze-drying treatment, a defatting treatment be carried out.

Next, DNA extraction from processed vegetable foods will be explained.

The extraction method includes fundamental DNA extraction methods, such as the above-described CTAB method, SDS-phenol method and protease K method. A desired method may be selected from these extraction methods and as the extraction conditions may be applied those described in the above literature.

There are no special conditions for these extraction methods but the phenol treatment in each of the methods is preferably carried out in more times than is described in the above literature in order to remove denatured protein.

In the case of the processed vegetable foods subjected to the protein denaturation treatment, which are the objects to which the present invention is applied, the DNA fraction obtained by extraction by the above method as it is sometimes cannot be utilized in a PCR method since they contain a PCR inhibitor.

For example, in the case of bean paste, the DNA is cut into lower molecules (i.e. lowering molecular weight of the DNA) by a nuclease derived from microorganisms used in the fermentation process and in this stage, low molecular DNA remains and is a cause for the inhibition of a PCR method.

In the case of steamed/boiled soybean, since it is subjected to a high temperature and high pressure treatment, DNA fragmentation occurs, so that it is necessary to remove the low molecular DNAs.

Parched soybean flour is produced by roasting at high temperatures for deactivating lectin, trypsin inhibitor, etc. contained in soybean seed and at the same time for imparting fragrance and by a subsequent finely pulverizing through mechanical grinding treatment.

As a result of passing such treatments, the double strands of DNA contained in the parched soybean flour is cut into low molecules to a level of nucleosome unit and the DNA linking the nucleosomes is fragmented to a size of several tens base pairs. In addition, during the process of finely pulverizing, samples are coated with oil in the state where nucleic acids and proteins are wrapped in cell fragments, and therefore use of the samples as they are in PCR, the action of buffer solution is not reached. For this reason, removal of very low molecular weight DNAs and removal of oil components are needed.

Further, in the case where the vegetable food used as a raw material is fermented soybeans, it is in a high viscosity state, as described above, due to contamination of DNA and polysaccharide derived from *B. subtilis* (natto-producing bacteria), and DNA of said *B. subtilis* (natto-producing bacteria) and DNA cut into lower molecules exist as mixtures, so that PCR amplification is inhibited considerably.

Accordingly, in the present invention, the DNA extracted by the above method is subjected to a treatment by a polyethylene glycol precipitation method and/or a DNA fractionation treatment by a polyacrylamide gel electrophoresis method to prepare DNA having a higher purity.

The treatment by a polyethylene glycol precipitation method includes a series operations of adding polyethylene glycol dissolved in a suitable solvent to a DNA extract solution by a conventional method and leaving it to stand, conducting solid-liquid separation by, for example, centrifugation, washing the separated precipitates, drying, removing the solvent, etc. This treatment gives purified DNA.

The treatment with polyacrylamide gel can be carried out in a conventional manner. For example, as shown in Examples hereinbelow, crude extract DNA is applied to a 2 mm thick 6.5% polyacrylamide gel and electrophoresed at 100 V, stained with 0.001% ethidium bromide for 10 minutes, then the gel in the target region is cut out under UV (320 nm) and DNA is extracted from the gel.

By these treatment, only DNAs having low molecules (on the order of about 200 base pairs) can remain.

The extraction treatment using a polyethylene glycol precipitation method and/or DNA fractionation treatment by a polyacrylamide gel electrophoresis method, for the reasons above, are operations which are recommended in the case where the target is vegetable foods containing remnant DNAs lower molecules, such as bean paste, steamed/boiled soybean, parched soybean flour, and fermented soybeans. In particular, when a food containing DNA extremely cut into lower molecules and much oil components such as parched soybean flour is used as a raw material, fractionation by these methods is necessary. In the case of steamed/boiled soybean, it is necessary to remove low molecular DNAs by conducting the operation of a polyethylene glycol precipitation method and thereafter extraction and purification using a polyacrylamide gel electrophoresis method.

In the case where the vegetable food used as a raw material is fermented soybeans (natto), it is desirable to conduct a DNA fractionation treatment by a polyacrylamide gel electrophoresis method for easy and ensured removal of inhibitors. With only the polyethylene glycol precipitation, PCR amplification may sometimes be inhibited considerably due to the occurrence of a high viscosity state caused by the polysaccharides produced by *B. subtilis* (natto-producing bacteria) and due to mixed presence of the DNA of *B. subtilis* (natto-producing bacteria) and the low molecular DNA thereof.

In this case, semi-preparatory gel electrophoresis using acrylamide, for example, may be used. This method can be applied to fermented soybeans and any other processed foods.

Of course, prior to the DNA fractionation treatment using a polyacrylamide gel electrophoresis method, the operation of extraction treatment by a polyethylene glycol precipitation method may be carried out.

As shown in later examples, when the raw material is fermented soybeans, the operation of DNA fractionation from the polyacrylamide gel enables one to obtain the target DNA by selecting fragments of 300 bp or less and purifying them.

In the case of raw materials other than fermented soybeans, the inhibitors can be removed easily and surely by carrying out the treatment.

In the method of the present invention, subsequent to the above-described treatment by a polyethylene glycol precipitation method and/or DNA fractionation treatment by a polyacrylamide gel electrophoresis method, the gel is further subjected to the Maxam-Gilbert method (Maxam, A. M. and Gilbert, W. (1977); A new method for sequencing DNA. Proc. Natl. Acad. Sci., 74, p560) or an electroelution method to extract a DNA fraction of the target size from the acrylamide gel, thereby further purifying the DNA.

For the conditions of extraction, for example, the gel is immersed in 0.001% ethidium bromide for 10 minutes and the gel of target region is cut out under UV (320 nm), and thereafter when the Maxam-Gilbert method is used, it is carried out under the conditions described in the above literature. On the other hand, in the case of electroelution method, the cut out gel and TE buffer solution are charged in a dialysis tube and current is applied at 100 V for 1 hour and the DNA eluted in the buffer solution in the tube is recovered.

In the case where the raw material is fermented soybeans (natto), it is desirable to perform this extraction treatment. By conducting this treatment, very low molecular DNA and fructan are mostly removed and DNA sufficiently purified for use as a template for PCR can be obtained.

Whether or not the DNA prepared by the extraction treatment and purification treatment as described above can be actually used as a template for PCR method can be confirmed by carrying out tests wherein the DNA is actually used as a template for a PCR method.

Upon practicing the tests, the present inventors have prepared 5 primers, that is, Act5', Act5'-2, Act5'-3, Act3', and Act3'-2 based on the gene sequence of β-actin of soybean on a database. The respective base sequences of the primers are shown in Seq. I.D. No. 1 to 5 in the Sequence Listing.

Figure 2:
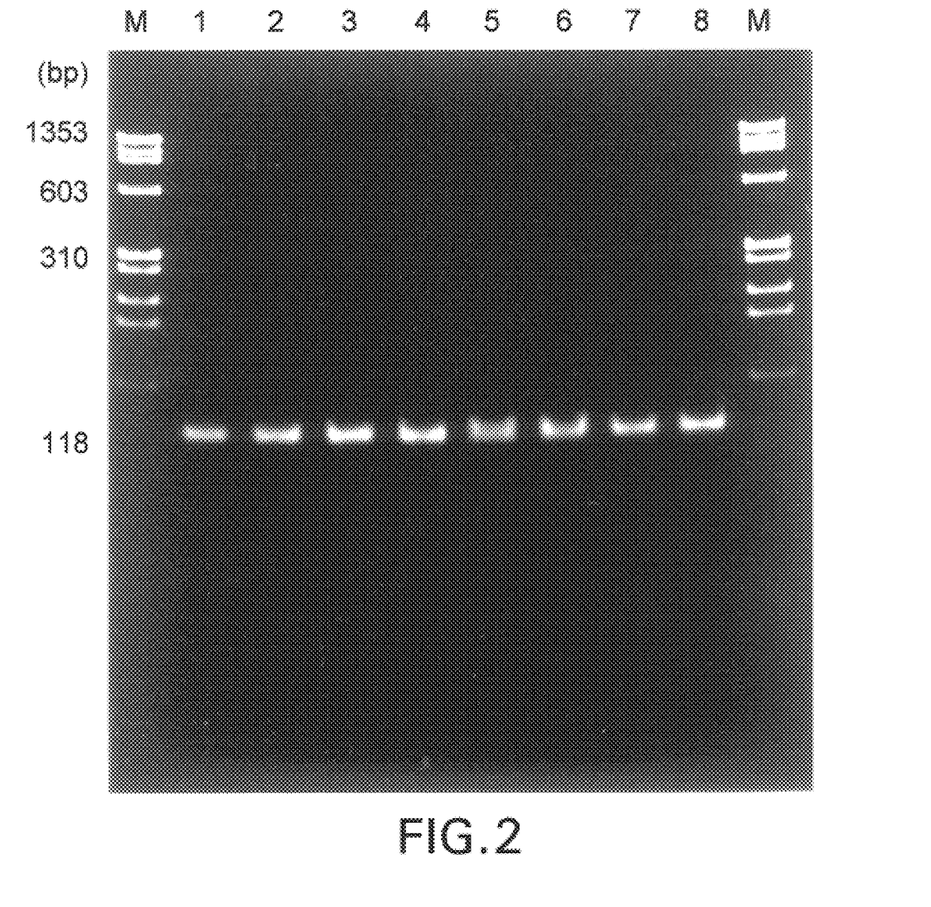
FIG. 2 is an electrophoretogram showing the results of PCR conducted using the DNAs of soybean processed foods, respectively, prepared in Production Example 1, in which character M in the upper part indicates a marker. Numerals 1 to 8 designate soybean seeds, soybean sprouts, soybean curd, fried soybean curd slice, steamed/boiled soybeans, parched soybean flour, bean paste, and fermented soybeans, respectively. Numerals on the left side represent molecular weights.

Using these primers, PCR in which the DNA prepared by the method of the present invention is employed was actually practiced and as a result, as shown in later examples, the polyacrylamide gel electrophoretogram of the PCR product was single (FIG. 2). This product was subcloned in pTA vector (manufactured by Invitrogen) to determine the base sequence and as a result it was identical to the sequence of β-actin.

This result indicates that the DNA prepared by the present invention is suitable as a template DNA for PCR reaction.

The method of the present invention can be used for judging recombinant gene incorporated in vegetable foods.

Hereafter, the method for detecting recombinant genes will be explained taking an example of Agrobacterium derived 5-enolpyruvylshikimate-3-phosphate synthase [EPSPS] (Padgett, S. R. et al. (1995); Development, identification, and characterization of a glyphosate-tolerant soybean line, Crop Sci., 1451–1461), which is the body of a herbicide-resistant gene incorporated in herbicide-resistant recombinant soybean, a typical example of recombinant plants put to practical use.

First, to clone the recombinant gene incorporated in a recombinant soybean, primers for the 35S promoter of cauliflower mosaic virus and for the terminator of NOS (nopaline synthetase) are prepared, respectively. Then, a PCR method is carried out using a DNA prepared from recombinant soybean as a template, and the primers thereof. The product is subcloned in pTA vector (manufactured by Invitrogen) and sequenced.

Based on the nucleic acid sequence of the cloned recombinant gene, a primer for detecting soybean seeds is constructed.

Out of the cloned recombinant genes, the present inventors prepared 4 primers corresponding to the above EPSPS, body of herbicide-resistant gene, i.e., EPSPS5'-1, EPSPS5'-2, EPSPS3'-1, and EPSPS3'-2. The base sequences of these primers are as shown in Seq. I.D. No. 6 to 9 in the Sequence Listing.

Using, out of the above primers, EPSPS5'-1 and EPSPS3'-1 as primers for detecting recombinant genes and using Act5' and Act3', primers of soybean β-actin, as primers for judging as to whether or not PCR amplification itself is going well, an ordinary PCR method (single step) is performed with a use of DNA prepared from recombinant soybean seeds by the method of the present invention as a template. In this case, detection is possible if the ratio of recombinant soybean is 0.1% ($1/1,000$).

The PCR can be performed under the conditions of 1 cycle of 96° C.—48 seconds, 66° C.—48 seconds, and 72° C.—1 minute, then 32 cycles of 94° C.—48 seconds, 66° C.—48 seconds, and 72° C.—1 minute, and then 72° C.—8 minutes.

Conducting 2-step PCR using a combination of primers EPSPS5'-1 and EPSPS3'-1 and a combination of EPSPS5'-2 and EPSPS3'-2 (the conditions of PCR for each step are the same as the above 1 step method), the detection of recombinant genes at a high sensitivity of 0.0001% ($1/1,000,000$) is possible. These results are shown in detail in later Test Example 2.

On the other hand, judgment of recombinant genes in processed foods from seeds of soybean, etc. as a raw material can be carried out as follows.

In this judgment, NOS5'-1 and NOS3'-1, primers the present inventors constructed, can be used between the 3' side of the EPSPS gene and the gene of the terminator of NOS (nopaline synthetase) incorporated downstream thereof. The base sequences of the primers are shown in Seq. I.D. Nos. 10 and 11 in the Sequence Listing, respectively.

By conducting PCR using the DNA extracted by the method of the present invention as a template and NOS5'-1 and NOS3'-1 as primers, recombinant genes can be detected from the processed foods using soybean as a raw material.

As the PCR conditions, usual conditions, for example, 1 cycle of 96° C.—48 seconds, 66° C.—48 seconds, and 72° C.—1 minute, then 40 cycles of 94° C.—48 seconds, 66° C.—48 seconds, and 72° C.—1 minute, and then 72° C.—8 minutes, are effective.

The reason for using the above primers is that particularly when recombinant genes from fermented soybeans is detected, the PCR product considered to be based on the EPSPS gene originated from B. subtilis (natto-producing bacteria) is detected by use of the above primers and primers at other sites.

Thus, use of the DNA prepared from vegetable foods by the method of the present invention as a template enables exact judgment as to the presence or absence of recombinant genes.

According to the method of the present invention, upon extraction of DNA from vegetable foods subjected to a protein denaturation treatment, defatting is carried out as a pretreatment, as needed, and further a treatment by a polyethylene glycol precipitation method and/or a DNA fractionation treatment by a polyacrylamide gel electrophoresis method and subsequent DNA extraction by the Maxam-Gilbert method or an electroelution method are used in combination, which enables extraction and preparation of high quality DNA, thereby being capable of constructing a suitable primer for use in a PCR method from the DNA.

The method of the present invention can be also applied to parched soybean flour subjected to a high temperature and mechanical grinding treatment, steamed/boiled soybean subjected to a high pressure treatment, and bean paste and fermented soybeans both subjected to fermentation operations. In particular, the method for extracting and preparing highly pure DNA from fermented soybeans was not established yet and has now been established by the present invention for the first time.

By selecting foods derived from recombinant crops as an object, the method of the present invention enables one to detect recombinant genes from the obtained highly pure DNA.

As for the sensitivity of detection of recombinant genes, conventional sensitivity of 0.1% recombinant soybean mixing is secured. Moreover, practicing a 2-stage PCR increases the sensitivity by 1,000 times.

As described above, when fermented soybeans are used as a raw material, after operations of DNA extraction, fractionation of DNA from polyacrylamide gel, and extraction of DNA by the Maxam-Gilbert method or electroelution method sequential thereto enable preparation of DNA which is feasible for PCR amplification, so that the method of the present invention has a significant practical value.

In addition, a feature of the present invention is residing in that a combination of primers which induces no non-specific band can also be constructed, which has a significant effect.

According to the present invention, there has been completed a method for extracting DNA having a purity sufficient for use as a template DNA in a PCR method from processed foods using oil source seeds as a material. This method is also effective for preparing a template DNA that makes it possible to conduct a PCR method for processed foods utilizing edible parts of a plant other than seeds, such as potato chips.

Furthermore, the method of the present invention can be utilized for preparing a template DNA which can be used in a PCR method for animal-derived foods derived from animals such as stock, the foods being processed by subjecting to a high temperature, high pressure treatment.

EXAMPLES

Hereafter, the present invention will be described in detail by examples. However, the present invention is not limited to these examples.

Production Example 1

Preparation of bean sprout, steamed/boiled soybean, soybean curd, fried soybean curd slice, and fermented soybeans (natto) as samples Using recombinant soybean seeds only or a mixture containing 10% of non-recombinant soybean seeds, bean sprout, steamed/boiled soybean, soybean curd, fried soybean curd slice, and fermented soybeans were prepared by the following methods.

Regarding Bean Sprouts

In a large stainless vat were placed 3 sheets of gauze one on another, which were wetted with water. Soybean seeds were sown on the wet gauze and light was shielded with aluminum foil against light and grown in the dark at room temperature for 7 days with daily exchange of water. The germs generated were collected to obtain samples.

Regarding Steamed/Boiled Soybean

Soybean seeds were allowed to absorb water at room temperature over one night and then subjected to autoclave treatment (121° C., 60 minutes) to prepare steamed/boiled soybean.

Regarding Soybean Curd and Fried Soybean Curd Slice

Soybean seeds were allowed to absorb water at a low temperature (about 18° C.) over one night and then crushed in a mixer and further ground with addition of water. After heating to about 95° C., this was filtered through a funnel in which was placed bleached cotton cloth to obtain tonyu (soy milk). The cake remaining on the bleached cotton cloth was squeezed to obtain additional portion of soy milk.

The soy milk portions were combined and cooled in a flowing water while stirring. Thereafter, a coagulant was added and the mixture was heated to coagulate, and cooled again in a flowing water to prepare soybean curd.

Fried soybean curd slice was prepared by slicing the thus prepared soybean curd and subsequent frying the slices with an edible oil.

Regarding Fermented Soybeans

Soybean seeds were allowed to absorb water at room temperature for one day and then subjected to autoclave treatment (121° C., 60 minutes) to steam/boil them. On the steamed/boiled soybean was sprayed Bacillus subtilis (natto-producing bacteria) and allowed to ferment at 42° C. for about 1 day to prepare fermented soybeans.

Regarding Parched Soybean Flour and Bean Paste

Commercial products were used for the both.

Example 1

DNA extraction (by SDS-phenol Method) from Soybean Seeds, Soybean Sprouts, Steamed/boiled Soybean, Soybean Curd, Fried Soybean Curd Slice, Parched Soybean Flour, and Bean Paste For soybean seeds, parched soybean flour, and bean paste, commercial products were used as samples. For soybean sprouts, steamed/boiled soybean, soybean curd, and fried soybean curd slice, the samples obtained in Production Example 1 above were used.

Each sample (excluding soybean seeds and soybean sprouts) was frozen in liquid nitrogen and then dried using a freeze-drier. Thereafter, the sample was ground in a mortar to form fine powder. This sample was defatted at 65° C. in a Soxhlet's extractor with diethyl ether. Using the defatted sample, DNA extraction was carried out.

The defatted sample (20 g) was homogenized after addition of 25 ml of buffer solution for extraction (100 mM Tris-HCl buffer solution, pH 8.8, containing 50 mM EDTA, 500 mM sodium chloride, and 10 mM β-mercaptoethanol) and 2.5 ml of 10% SDS was added to the homogenate and incubated at 65° C. for 15 minutes.

Then, potassium acetate was added to a final concentration of 1 M and the mixture was left to stand on ice for 30 minutes. Thereafter, the mixture was centrifuged under the conditions of 10,000×g, 10 minutes, and 4° C. to obtain a supernatant. To the supernatant was added phenol saturated with the equivalent amount of TE (10 mM Tris-HCl buffer solution, pH 8.0, containing 1 mM EDTA, pH 8.0), mixed and then centrifuged under the same conditions as above to obtain a water layer. The operation of extraction with phenol was repeated 3 times.

Thereafter, similar operations were conducted with replacing phenol by diethyl ether and the phenol dissolved in the water layer was extracted with ether.

The water layer after the extraction with ether was added 0.6 time volume of isopropyl alcohol and the mixture was left to stand at room temperature for 20 minutes. Thereafter, it was centrifuged under the conditions of 10,000×g, 10 minutes, and 4° C. to obtain precipitates. The precipitates were washed with 70% (v/v) ethanol, dried and removed of ethanol, and then dissolved in 5 ml of TE.

To the solution was added RNase A to a final concentration of 0.05 mg/ml and the mixture was incubated at 37° C. for 1 hour to decompose the RNA in the sample. Thereafter, similarly to the above, the operations of extraction with phenol and extraction with ether were conducted.

In the case of soybean seeds, soybean sprouts, soybean curd and fried soybean curd slice, samples of the DNA fractions thus obtained were used in PCR.

For the samples of steamed/boiled soybeans, parched soybean flour and bean paste, to the water layer obtained by the above method was added 20% (w/v) polyethylene glycol—6,000(PEG-6,000) dissolved in a 0.6 time amount of 2.5 M sodium chloride solution and the mixture was left to stand on ice for at least 1 hour. Thereafter, the mixture was centrifuged under the conditions of 10,000×g, 10 minutes, and 4° C. to obtain precipitates.

The precipitates were washed with 70% (v/v) ethanol, dried and removed of ethanol, and then dissolved in 1 ml of sterilized water to obtain a DNA solution. For the steamed/boiled soybeans, fractionation of DNA length by polyacrylamide gel electrophoresis was also conducted.

Example 2

Extraction of DNA from Fermented Soybeans

To sterilize *B. subtilis* (natto-producing bacteria), heat sterilization treatment was practiced under the conditions of 121° C. and 60 minutes. Thereafter, extraction of DNA was tried according to the method same as those in Example 1.

However, the obtained DNA solution was high in viscosity and in addition polysaccharides and the like secreted from *B. subtilis* (natto-producing bacteria) are contained in large amounts, so that DNA suitable for PCR reaction was not obtained.

Accordingly, removal of the polysaccharides, etc. from the above DNA solution using a polyacrylamide gel electrophoresis method was tried.

Figure 1:
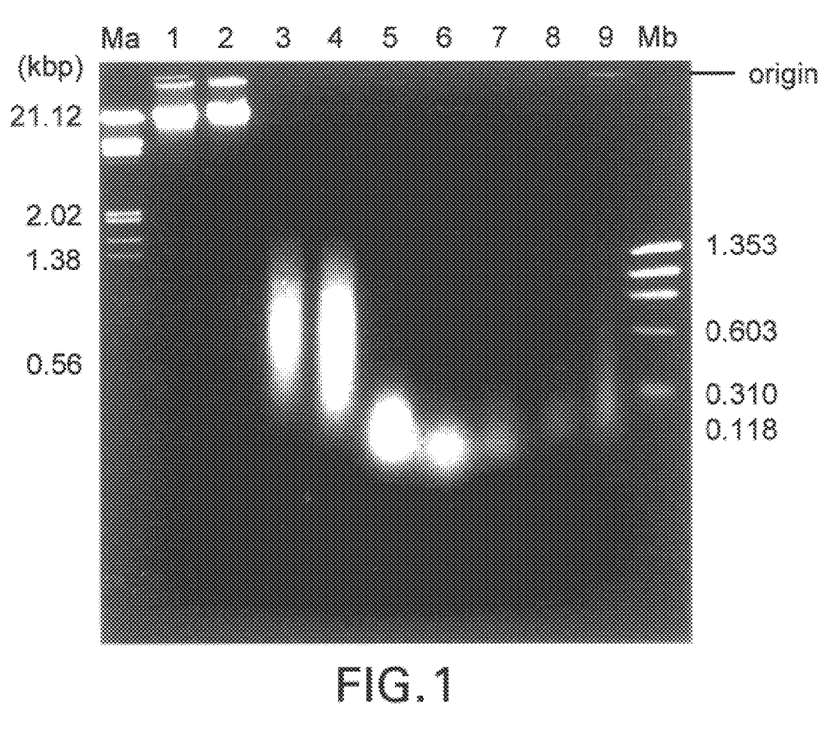
FIG. 1 is an electrophoretogram showing the molecular weights of the DNAs of soybean processed foods, respectively, prepared in Production Example 1, in which characters Ma and Mb in the upper part indicate markers. Numerals 1 to 9 designate soybean seeds, soybean sprouts, soybean curd, fried soybean curd slice, steamed/boiled soybeans, parched soybean flour, bean paste, fermented soybean fraction III, and fermented soybeans, respectively. Numerals on the right and left sides both represent molecular weights.

As a result of practicing the polyacrylamide gel electrophoresis method, a high molecular DNA derived from *B. subtilis* (natto-producing bacteria) and low molecular DNAs derived from soybean presumably decomposed were observed though slightly (cf. Lane 9 in FIG. 1). Therefore, fractionation of DNA length was practiced using polyacrylamide gel. The fractionation of the DNA of fermented soybeans was conducted by dividing the sample into three fractions of 600 bp or more (Fermented soybean I), from 300 bp to 600 bp (Fermented soybean II), and 300 bp or less (Fermented soybean III).

That is, 450 µg equivalent of sample DNA obtained by conducting the polyethylene glycol precipitation in the same manner as in Example 1 was placed on a 6.5% polyacrylamide gel of 2 mm thick and electrophoresis was carried out at 100 V. After the electrophoresis, the gel was stained with ethidium bromide and then fractionated to three fractions of 600 bp or more (Fermented soybean I), from 300 bp to 600 bp (Fermented soybean II), and 300 bp or less (Fermented soybean III), which were cut out from the polyacrylamide gel.

To recover DNA from the cut out gels, extraction of DNA based on the Maxam-Gilbert method was carried out. That is, the cut out gels were crushed with a sterilized glass rod until paste was obtained. Then, 0.2 ml of buffer solution for extraction (0.5 M ammonium acetate, 10 mM magnesium acetate, 2.5 mM EDTA, 0.1% SDS) was added and mixed vigorously for about 30 seconds using a vortex mixer. Thereafter, the mixture was centrifuged under the conditions of 15,000×g, 10 minutes, and 4° C. to obtain a supernatant. This extraction operation was repeated twice to extract DNA from the gel.

After completion of the extraction operation, the extracts were combined and extraction with ether was carried out after extraction with phenol in the same manner as in Example 1. To the water layer after the extraction was added 2 times volume of ethanol and the mixture was cooled at −20° C. for 30 minutes, followed by centrifugation under the conditions of 15,000×g, 15 minutes, and 4° C. to obtain precipitates.

After washing with 70% (v/v) ethanol, the precipitates were dried and then dissolved in 30 ml of sterilized water to obtain purified DNA.

As an alternative method, the operations subsequent to the above phenol extraction may be carried out after practicing the above electroeluting method, etc. instead of the Maxam-Gilbert method.

The DNA extracted from the fraction of 300 bp or less (Fermented soybean III) was subjected to electrophoresis test and as a result a dim band was observed (cf. Lane 8 in FIG. 1).

Test Example 1

Study was made as to whether or not a PCR method is possible in which DNAs extracted from soybean seeds, soybean sprouts, steamed/boiled soybeans, soybean curd, fried soybean curd slice, parched soybean flour, and bean paste are used as a template.

PCR was practiced using soybean β-actin primers (Act5'-2 (cf. Seq. I.D. No. 2 in the Sequence Listing) and Act3' (cf. Seq. I.D. No. 4 in the Sequence Listing); 0.05 µM) under the conditions of 1 cycle of 96° C.—48 seconds, 66° C.—48 seconds, and 72° C.—1 minute, then 32 cycles of 94° C.—48 seconds, 66° C.—48 seconds, and 72° C.—1 minute, and then 72° C.—8 minutes.

As a result, as shown in FIG. 2, bands were confirmed for all the DNA samples.

Further, upon practice of 2-stage PCR (first PCR: primer Act5'-2 (cf. Seq. I.D. No. 2 in the Sequence Listing), Act 3' (cf. Seq. I.D. No. 4 in the Sequence Listing); 0.05 µM, the conditions of PCR were the same as above, second PCR: primer Act5'-3 (cf. Seq. I.D. No. 3 in the Sequence Listing), Act 3'-2 (cf. Seq. I.D. No. 5 in the Sequence Listing); 0.05 µM, the conditions of PCR were the same as above), bands were confirmed for all the DNA samples. In the case of fermented soybeans, PCR method was possible only with the DNA obtained from the fraction of 300 bp or less (Fermented soybean III).

From this, it was found that with a use of the DNA extracted and prepared from steamed/boiled soybean, fermented soybeans, parched soybean flour, and bean paste by a series of operations in Production Example 1, PCR method is possible as in the case of the DNA extracted from the raw materials which were not subjected to the protein denaturation treatment, such as soybean seeds and soybean sprouts.

In particular, it is very interesting that DNA which can be used for the detection of a PCR method, can be prepared from parched soybean flour which has been subjected to a high temperature treatment and a mechanical grinding treatment, and from fermented soybeans, bean paste, etc. which have been subjected to fermentation process.

Test Example 2

Detection of Recombinant Genes

Using 100 ng of DNA extracted from genetic recombinant soybean seeds, the detection limit of a PCR method was studied.

Primers for 5-enolpyruvylshikimate-3-phosphate synthase (EPSPS) (EPSPS5'-1 (cf. Seq. I.D. No. 6 in the Sequence Listing), EPSPS3'-1 (cf. Seq. I.D. No. 8 in the Sequence Listing); 0.1 μM) were prepared.

As primers for β-actin gene of soybean used for judging if PCR reaction proceeds smoothly, a pair of primers (Act5' (cf. Seq. I.D. No. 1 in the Sequence Listing), Act3' (cf. Seq. I.D. No. 4 in the Sequence Listing); 0.05 μM) were used.

Using these 4 kinds of primers and the DNA extracted from the recombinant soybean seeds prepared in Test Example 1 above as a template, PCR was performed for detection of recombinant genes.

The conditions of PCR were the same as in Test Example 1 (1 cycle of 96° C.—48 seconds, 66° C.—48 seconds, and 72° C.—1 minute, then 32 cycles of 94° C.—48 seconds, 66° C.—48 seconds, and 72° C.—1 minute, and then 72° C.—8 minutes).

As a result, the detection was possible even with the sample having a recombinant soybean ratio of 0.1% (1/1,000).

Further, 2-stage PCR (first PCR: primer EPSPS5'-1 (cf. Seq. I.D. No. 6 in the Sequence Listing), EPSPS3'-1 (cf. Seq. I.D. No. 8 in the Sequence Listing); 0.1 μM, the conditions of PCR were the same as above, second PCR: primer EPSPS5'-2 (cf. Seq. I.D. No. 7 in the Sequence Listing), EPSPS3'-2 (cf. Seq. I.D. No. 9 in the Sequence Listing); 0.1 μM, the conditions of PCR were the same as above) was performed.

As a result, the detection was possible even with the sample having a recombinant soybean ratio of 0.0001% (1/1,000,000), and it was shown that detection with high sensitivity was possible.

From the results, it is apparent that the method of DNA extraction according to the method of the present invention and the DNA prepared by this method are very useful for detecting recombinant genes by a PCR method.

Test Example 3

Next, using the DNA extracted and prepared from soybean sprouts, steamed/boiled soybeans, soybean curd, fried soybean curd slice, and fermented soybeans, all of which were prepared from recombinant soybeans, detection of recombinant genes was performed. For the parched soybean flour and bean paste were used commercial products and hence there was no negative control nor positive control so that detection of recombinant genes was not performed.

As the primers, NOS5'-1 (cf. Seq. I.D. No. 10 in the Sequence Listing) and NOS3'-1 (cf. Seq. I.D. No. 11 in the Sequence Listing) were constructed between the 3' side of the EPSPS gene and the gene of the terminator of NOS (nopaline synthetase) incorporated downstream thereof.

Using 0.1 μM of each primer and the DNA extracted from the above foods as a template, a PCR method was carried out. The conditions of PCR were 1 cycle of 96° C.—48 seconds, 66° C.—48 seconds, and 72° C.—1 minute, then 50 cycles of 94° C.—48 seconds, 66° C.—48 seconds, and 72° C.—1 minute, and then 72° C.—8 minutes.

As primers for β-actin gene of soybean used for judging if PCR reaction proceeds smoothly, a pair of primers (Act5' (cf. Seq. I.D. No. 1 in the Sequence Listing), Act3' (cf. Seq. I.D. No. 4 in the Sequence Listing); 0.05 μM) were used.

Figure 3:
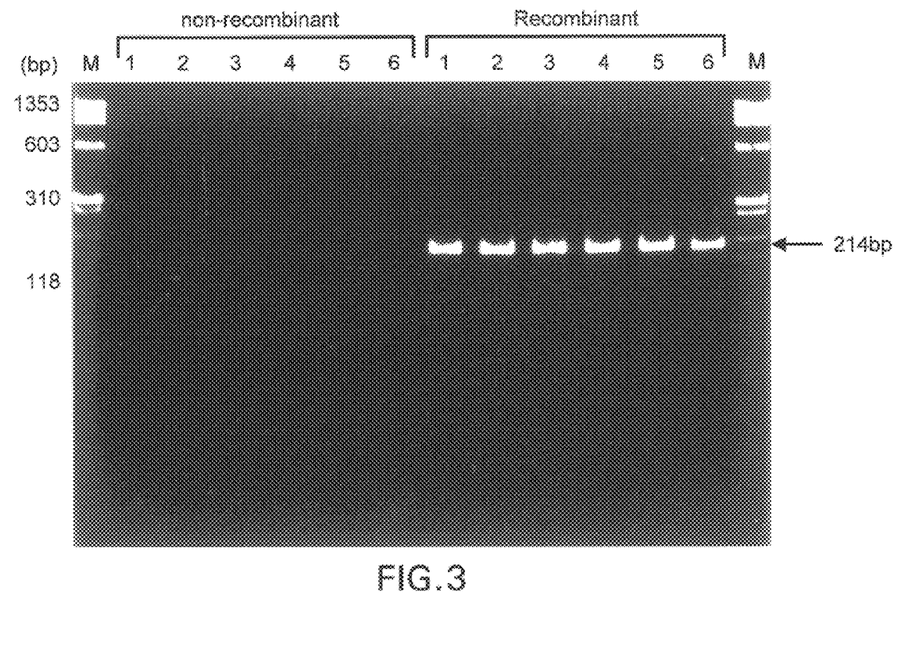

As a result, as shown on the right hand side in FIG. 3, using the DNA extracted and prepared by the method of the present invention from steamed/boiled soybean, soybean curd, fried soybean curd slice and fermented soybeans all of which were prepared from recombinant soybeans as a raw material, the recombinant genes could be detected on a level equivalent to that obtained in the case of the recombinant soybean seeds and recombinant soybean sprouts.

Among them, in particular, detection of recombinant genes from fermented soybeans has not been reported yet.

What is claimed is:

1. A method for preparing a template DNA from a processed vegetable food, comprising:

said processed vegetable food, having been subjected to a protein denaturation treatment as a component of the processing necessary to prepare processed vegetable food, subsequently defatting processed vegetable food;

extracting a crude DNA fraction from said defatted processed vegetable food; and performing a DNA purification treatment of the crude DNA fraction by polyethylene glycol precipitation, or by a DNA fractionation treatment using polyacrylamide gel electrophoresis or by a combination thereof.

2. The method as claimed in claim 1, wherein the processed vegetable food is an oil source seed.

3. The method of claim 1, wherein said processed vegetable food is one which is obtained from soybean, rice, wheat, corn or potato.

4. A method for detecting a gene of a plant in a processed food derived from said plant, comprising:

analyzing the template DNA prepared by the method of claim 1 by a PCR method thereby detecting said gene.

5. A method for preparing a template DNA from a processed vegetable food, comprising:

said processing vegetable food, having been subjected to a protein denaturation treatment as a component of the processing necessary to prepare processed vegetable food, subsequently defatting said processed vegetable food by solvent extraction by the Soxhlet method or by defatting the processed vegetable food with ether;

extracting a crude DNA fraction from said defatted processed vegetable food; and performing a DNA purification treatment of the crude DNA fraction by polyethylene glycol precipitation, or by a DNA fractionation treatment using polyacrylamide gel electrophoresis or by a combination thereof.

* * * * *

UNITED STATES PATENT AND TRADEMARK OFFICE
CERTIFICATE OF CORRECTION

PATENT NO. : 6,492,114 B2
DATED : December 10, 2002
INVENTOR(S) : Arahira et al.

It is certified that error appears in the above-identified patent and that said Letters Patent is hereby corrected as shown below:

<u>Title page,</u>
Item [73], Assignee, should read:

-- [73] Assignee: Director of National Food Research Institute, Ministry of Agriculture, Forestry and Fisheries, Tsukuba (JP) --

Signed and Sealed this

Nineteenth Day of August, 2003

JAMES E. ROGAN
*Director of the United States Patent and Trademark Office*